US00PP22658P3

(12) United States Plant Patent
Blom

(10) Patent No.: US PP22,658 P3
(45) Date of Patent: Apr. 17, 2012

(54) ***CHRYSANTHEMUM* PLANT NAMED 'ZANMUCANDLE'**

(50) Latin Name: *Chrysanthemum×morifolium Ramat.*
Varietal Denomination: Zanmucandle

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 166 days.

(21) Appl. No.: 12/591,869

(22) Filed: Dec. 3, 2009

(65) Prior Publication Data

US 2011/0138510 P1 Jun. 9, 2011

(51) Int. Cl.
*A01H 5/00* (2006.01)

(52) U.S. Cl. ..... Plt./287

(58) Field of Classification Search ..... Plt./287, Plt./289, 294
See application file for complete search history.

(56) References Cited

U.S. PATENT DOCUMENTS

| | | | | |
|---|---|---|---|---|
| PP11,991 | P2 * | 7/2001 | Flint | Plt./287 |
| PP12,528 | P2 * | 4/2002 | Bergman | Plt./287 |
| PP13,463 | P2 * | 1/2003 | Vandenberg | Plt./289 |
| PP20,473 | P3 * | 11/2009 | Blom | Plt./288 |

* cited by examiner

*Primary Examiner* — Wendy C Haas
(74) *Attorney, Agent, or Firm* — Steptoe & Johnson LLP

(57) ABSTRACT

A *chrysanthemum* plant named 'Zanmucandle' characterized by its large sized blooms with white ray florets and prolific branching; natural season flower date August 17-21; blooming for a period of 5 weeks.

3 Drawing Sheets

Botanical designation: *Chrysanthemum×morifolium* Ramat.

Variety denomination: 'Zanmucandle'.

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmucandle'. 'Zanmucandle' is a product of a breeding and selection program for outdoor pot mums (garden mums) which had the objective of creating new cultivars with a double type inflorescence, a natural season flower date starting at August 17-21, blooming for a period of 5 weeks. 'Zanmucandle' is a seedling resulting from the crossing between the female parent id 4910 and the male parent id 2648, both unpatented plants. Plants of 'Zanmucandle' differ from plants of the female parent in the color of the ray-florets: that of the seedling is white while the color of the female parent is yellow. The differences between plants of 'Zanmucandle' and plants of the male parent are (1) Natural season flower date and (2) Inflorescence size. (1) The seedling flowers one to two weeks earlier. (2) The inflorescence size is larger in the seedling.

The new and distinct cultivar was discovered and selected as a flowering plant by Wilhelmus Bernardus Blom on a cultivated field in Rijsenhout, The Netherlands in 2005. The first act of asexual production of 'Zanmucandle' was accomplished when vegetative cuttings from the initial selection in 2005 were used and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
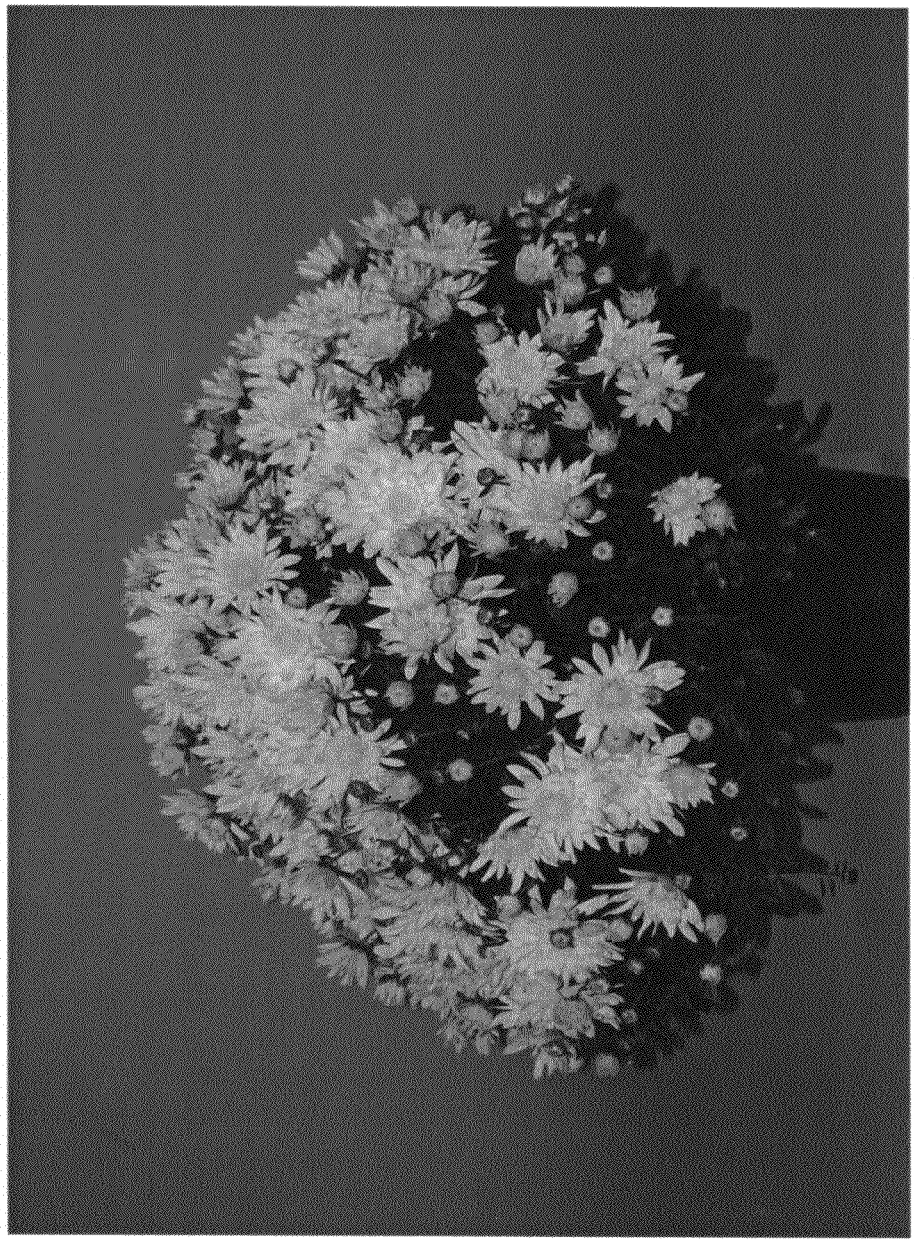
FIG. 1 shows a plant of the cultivar in full bloom.
Figure 2:
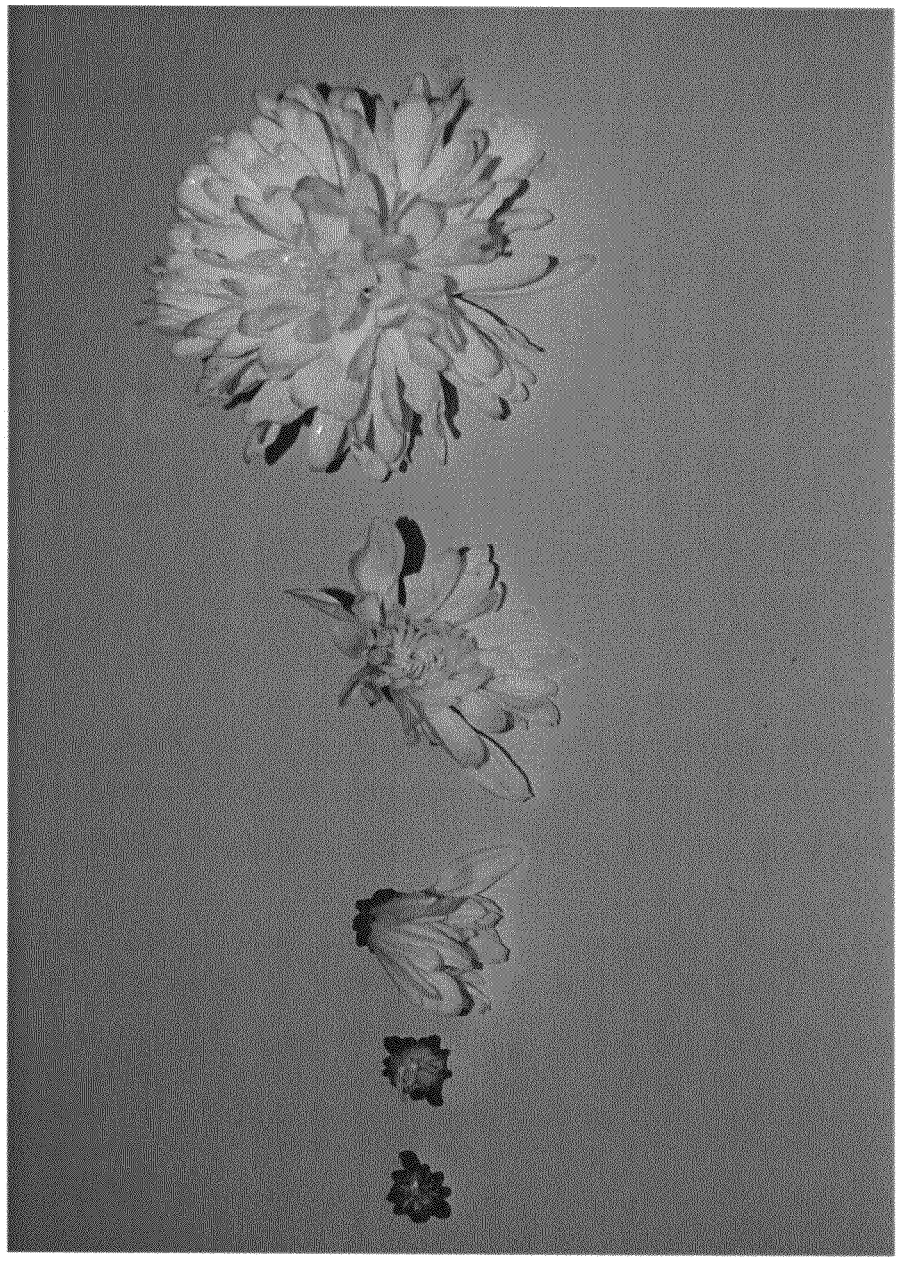
FIG. 2 shows the various stages of bloom of the new cultivar.
Figure 3:
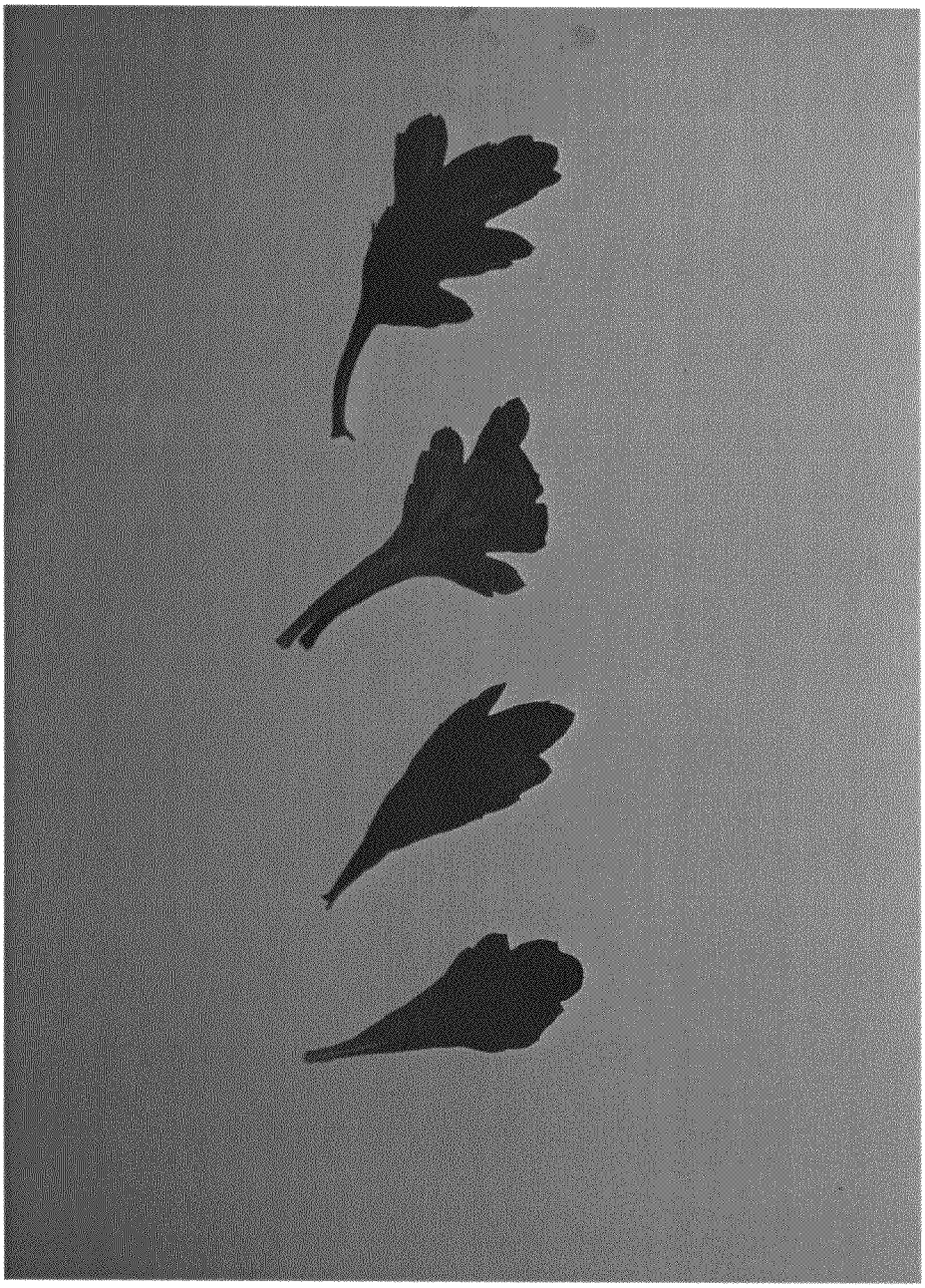
FIG. 3 shows the various stages of foliage of the new cultivar.

The observations and measurements were gathered from plants grown out door in Rijsenhout, The Netherlands under natural day length and temperature and planted in week 25 in 2009. The natural blooming date of this crop was August 17-21 . The average height of the plants was 16 cm. No growth retardants were used. No tests were done on disease or insect resistance or susceptibility. No tests were done on cold or drought tolerance. This new variety produces large sized blooms with white ray florets blooming for a period of 5 weeks.

From the cultivars known to inventor the most similar existing cultivar in comparison to 'Zanmucandle' is 'Zanmustarbu' (U.S. Plant Pat. No. 20,473). When 'Zanmustarbu' and 'Zanmucandle' are being compared the following difference is noticed: The difference of 'Zanmustarbu' and 'Zanmucandle' are (1) number ray-florets and (2) length ray-florets. (1) The number is lower in 'Zanmucandle'. (2) Ray-florets of 'Zanmucandle' are longer. The following is a description of the plant and characteristics that distinguish 'Zanmucandle' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

DETAILED BOTANICAL DESCRIPTION

Bud:
- *Size.*—Small; cross-section 0.5 cm, height 0.5 cm.
- *Shape.*—Round.
- *Texture.*—Pubescent.
- *Outside color.*—Greyed-green 191A.

Phyllaries:
- *Number.*—22, arranged in 2 rows.
- *Shape.*—Elliptic.
- *Apex.*—Acute.
- *Base.*—Truncate.
- *Margin.*—Entire.
- *Color.*—Upper surface Greyed-green 191A.
- *Length and width.*—5 mm; 2 mm.
- *Texture.*—Pubescent.

Inflorescence:
- *Type.*—Double.
- *Height.*—2 cm.
- *Diameter.*—6.5 cm.
- *Peduncle length.*—6 cm.
- *Peduncle color.*—Greyed-green 191C.
- *Peduncle diameter.*—1.5 mm.
- *Peduncle texture.*—Pubescent.
- *Number per branch.*—Approx. 5 inflorescences.
- *Duration of flowering.*—5 weeks.
- *Seeds.*—Produced in small quantities, ovate, Greyed-brown 199A, length 1.5 mm, diameter 0.8 mm.
- *Fragrance.*—Faint *chrysanthemum* odor.

Color:
- *Center of inflorescence.*—Immature stage: Yellow 9A. Mature stage: Yellow 9A.
- *Color of upper surface of the ray-florets.*—White 155D.
- *Color of the lower surface of the ray-florets.*—White 155D.
- *Tonality from distance.*—A garden mum with white flowers and a cream center.
- *Color of the ray-florets after aging of the plant.*—White 155D.

Ray florets:
- *Texture.*—Upper and lower surface smooth.
- *Number.*—155-165.
- *Shape.*—Narrowly elliptic.
- *Apex.*—Pointed.
- *Base.*—Attenuate.
- *Cross-section.*—Convex.
- *Longitudinal axis of majority.*—Reflexing.
- *Length of corolla tube.*—3-4 mm.
- *Ray-floret margin.*—Entire.
- *Ray-floret length.*—3-4 cm.
- *Ray-floret width.*—4-5 mm.
- *Ratio length/width.*—High.

Disc florets: Absent

Receptacle:
- *Color.*—Green 138C.
- *Shape.*—Conical raised.
- *Height.*—0.5 cm.
- *Diameter.*—0.7 cm.

Reproductive organs:
- *Androecium.*—Absent.
- *Pollen.*—Absent.
- *Gynoecium.*—Present on ray-florets.
- *Style color.*—Yellow-green 154C.
- *Style length.*—3 mm.
- *Stigma color.*—Yellow 7A.
- *Stigma width.*—1 mm.
- *Ovary.*—Enclosed in calyx.

Plant:
- *Form.*—Grown as a spray type pot mum, outdoor raised and mounded.
- *Growth habit.*—Loosely spreading, somewhat spherical shape.
- *Growth rate.*—Low.
- *Height.*—16 cm.
- *Width.*—30 cm.
- *Stem color.*—Greyed-brown 199A.
- *Stem strength.*—Weak.
- *Stem brittleness.*—Brittle.
- *Stem anthocyanin coloration.*—Not observed.
- *Internode length.*—2 cm.
- *Length of lateral branch.*—From top to bottom 15-16 cm.
- *Lateral branch color.*—Green 137 C.
- *Lateral branch brittleness.*—Brittle.
- *Lateral branch diameter.*—2.2 mm.
- *Branching* (*average number of lateral branches*).—Prolific with 8 breaks after pinching.
- *Natural season blooming date.*—August 17-21.

Foliage:
- *Leaf color.*—Upper side: Green 138A. Lower side: Green 138B.
- *Color midvein.*—Upper side: Yellow-green 147D. Lower side: Yellow-green 148D.
- *Size.*—Small.; length 3.5-4.5 cm, width 1.4-1.7 cm.
- *Quantity* (*number per lateral branch*).—28-32.
- *Shape.*—Elliptic.
- *Texture upper side.*—Sparsely pubescent.
- *Texture under side.*—Pubescent.
- *Venation arrangement.*—Palmate.
- *Shape of the margin.*—Serrated.
- *Shape of base of sinus between lateral lobes.*—Rounded.
- *Margin of sinus between lateral lobes.*—Diverging.
- *Shape of base.*—Attenuate to Acute.
- *Apex.*—Mucronulate.
- *Petiole length.*—3 mm.
- *Petiole diameter.*—2 mm.
- *Petiole color.*—Yellow-green 147D.

TABLE 1

| Differences with the comparison variety | | |
|---|---|---|
| | 'Zanmucandle' | 'Zanmustarbu' |
| Number ray-florets | 155-165 | 180-200 |
| Length ray-florets | 3-4 cm | 2-3.5 cm |

I claim:

1. A new and distinct *chrysanthemum* plant named 'Zanmucandle' as described and illustrated.

* * * * *